United States Patent
Frigg et al.

(10) Patent No.: US 6,945,972 B2
(45) Date of Patent: Sep. 20, 2005

(54) APPARATUS FOR CONNECTING A BONE FASTENER TO A LONGITUDINAL ROD

(75) Inventors: Robert Frigg, Bettlach (CH); Raoul Donath, Grenzach-Wyhlou (DE)

(73) Assignee: Synthes, Paoli, PA (US)

( * ) Notice: Subject to any disclaimer, the term of this patent is extended or adjusted under 35 U.S.C. 154(b) by 0 days.

(21) Appl. No.: 10/372,345

(22) Filed: Feb. 24, 2003

(65) Prior Publication Data

US 2003/0149432 A1 Aug. 7, 2003

Related U.S. Application Data

(63) Continuation of application No. PCT/CH00/00449, filed on Aug. 24, 2000.

(51) Int. Cl.⁷ .................................................. A61B 17/58
(52) U.S. Cl. ....................................................... 606/61
(58) Field of Search ............................. 606/61, 60, 70, 606/71, 72, 69, 73

(56) References Cited

U.S. PATENT DOCUMENTS

| | | |
|---|---|---|
| 4,946,458 A | 8/1990 | Harms et al. |
| 5,002,542 A | 3/1991 | Frigg |
| 5,176,680 A | 1/1993 | Vignaud et al. |
| 5,207,678 A | 5/1993 | Harms et al. |
| 5,261,909 A | 11/1993 | Sutterlin et al. |
| 5,352,226 A | 10/1994 | Lin |
| 5,429,639 A | 7/1995 | Judet |
| 5,443,467 A | 8/1995 | Biedermann et al. |
| 5,466,237 A | 11/1995 | Byrd, III et al. |
| 5,474,551 A | 12/1995 | Finn et al. |
| 5,474,555 A | 12/1995 | Puno et al. |
| 5,487,744 A | 1/1996 | Howland |
| 5,499,983 A | 3/1996 | Hughes |
| 5,501,684 A * | 3/1996 | Schlapfer et al. ............. 606/73 |
| 5,520,690 A | 5/1996 | Errico et al. |
| 5,527,314 A | 6/1996 | Brumfield et al. |
| 5,531,746 A | 7/1996 | Errico et al. |

(Continued)

FOREIGN PATENT DOCUMENTS

| | | | |
|---|---|---|---|
| DE | 195 09 332 | 3/1995 | |
| DE | 195 22 114 | 6/1995 | |
| DE | 4414782 | * 11/1995 | ................. 606/61 |
| EP | 0 242 708 | 8/1987 | |
| EP | 0 330 881 | 10/1989 | |
| EP | 0 441 729 | 8/1991 | |
| FR | 2 794 962 A | 12/2000 | |
| WO | WO 94/00066 | 1/1994 | |
| WO | WO9621396 | * 7/1996 | ................. 606/61 |
| WO | WO 97/02786 | 1/1997 | |
| WO | WO 98/34554 | 8/1998 | |
| WO | WO 00/15125 | 3/2000 | |
| WO | WO 00/76412 | 12/2000 | |
| WO | WO 02/15806 | 2/2002 | |

*Primary Examiner*—Pedro Philogene
(74) *Attorney, Agent, or Firm*—Jones Day

(57) ABSTRACT

A device for connecting a bone fastener to a longitudinal rod is disclosed. The apparatus may have two bores spaced a distance apart and having generally parallel axes. A holding member may be associated with one bore, the member configured to engage a bone fastener such as a bone screw or pedicle hook. A rod coupling member may be associated with the other bore, the member configured to engage a longitudinal rod. The holding member and rod coupling member both are configured to articulate within their respective bores, thus allowing the rod and rod coupling, as well as the holding member and bone fastener, to rotate about the both the first and second axes. The holding member and rod coupling member further may be separately lockable to allow independent locking of the bone fastener and the rod to the connector, thereby preventing or enabling relative rotation as desired.

16 Claims, 3 Drawing Sheets

U.S. PATENT DOCUMENTS

| | | |
|---|---|---|
| 5,534,001 A | 7/1996 | Schlapfer et al. |
| 5,549,608 A | 8/1996 | Errico et al. |
| 5,554,157 A | 9/1996 | Errico et al. |
| 5,575,791 A | 11/1996 | Lin |
| 5,575,792 A | 11/1996 | Errico et al. |
| 5,578,033 A | 11/1996 | Errico et al. |
| 5,584,834 A | 12/1996 | Errico et al. |
| 5,586,984 A | 12/1996 | Errico et al. |
| 5,591,166 A | 1/1997 | Bernhardt et al. |
| 5,607,426 A | 3/1997 | Ralph et al. |
| 5,609,593 A | 3/1997 | Errico et al. |
| 5,609,594 A | 3/1997 | Errico et al. |
| 5,647,873 A | 7/1997 | Errico et al. |
| 5,669,911 A | 9/1997 | Errico et al. |
| 5,672,176 A | 9/1997 | Biedermann et al. |
| 5,683,392 A | 11/1997 | Richelsoph et al. |
| 5,688,273 A | 11/1997 | Errico et al. |
| 5,690,630 A | 11/1997 | Errico et al. |
| 5,713,898 A * | 2/1998 | Stucker et al. ............. 606/60 |
| 5,728,098 A | 3/1998 | Sherman et al. |
| 5,733,285 A | 3/1998 | Errico et al. |
| 5,735,853 A | 4/1998 | Olerud |
| 5,741,255 A | 4/1998 | Krag et al. |
| 5,752,957 A | 5/1998 | Ralph et al. |
| 5,782,831 A | 7/1998 | Sherman et al. |
| 5,782,833 A | 7/1998 | Haider |
| 5,797,911 A | 8/1998 | Sherman et al. |
| 5,810,819 A | 9/1998 | Errico et al. |
| 5,817,094 A | 10/1998 | Errico et al. |
| 5,863,293 A | 1/1999 | Richelsoph |
| 5,879,350 A | 3/1999 | Sherman et al. |
| 5,928,233 A * | 7/1999 | Apfelbaum et al. .......... 606/61 |
| 6,063,090 A | 5/2000 | Schläpfer |
| 6,132,432 A | 10/2000 | Richelsoph |
| 6,187,005 B1 | 2/2001 | Brace et al. |
| 6,235,033 B1 * | 5/2001 | Brace et al. ................. 606/69 |
| 6,248,105 B1 | 6/2001 | Schlapfer |
| 6,413,257 B1 | 7/2002 | Lin et al. |
| 6,524,315 B1 * | 2/2003 | Selvitelli et al. .............. 606/70 |
| 2003/0028191 A1 | 2/2003 | Shluzas |

* cited by examiner

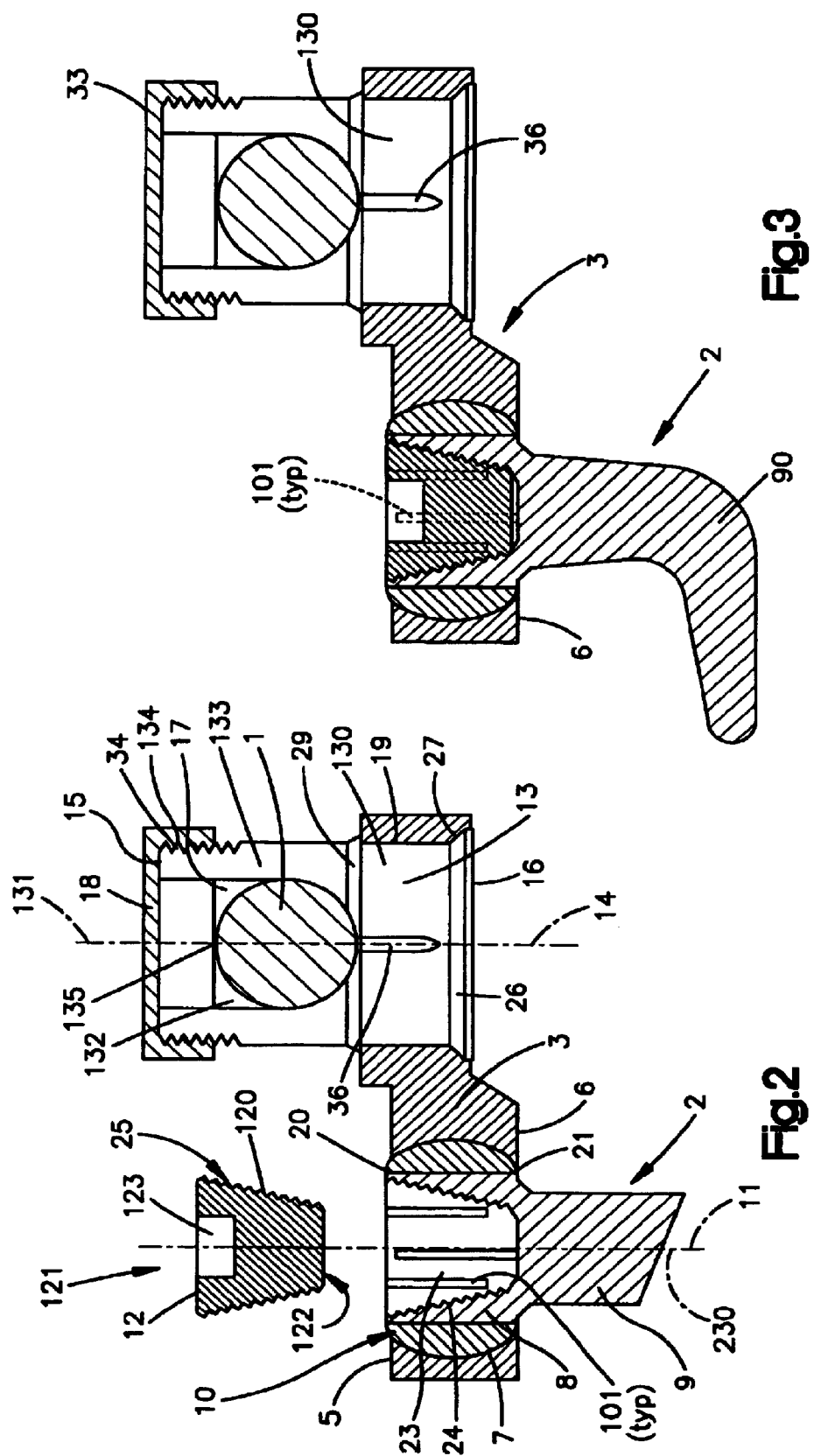

APPARATUS FOR CONNECTING A BONE FASTENER TO A LONGITUDINAL ROD

CROSS-REFERENCE TO RELATED APPLICATIONS

This application is a continuation of the US National Phase designation of co-pending international patent application No. PCT/CH00/00449, filed Aug. 24, 2000, the entire content of which is expressly incorporated herein by reference thereto.

FIELD OF THE INVENTION

The present invention relates to spinal fixation systems and, in particular, to a device for adjustably connecting a bone fastener to a longitudinal rod.

BACKGROUND OF THE INVENTION

In the posterior treatment of spinal deformities, pedicle screws or hooks are used to connect vertebral bodies to a longitudinal rod. Prior to implantation, the longitudinal rod is shaped in a particular form so as to correct the deformity of the vertebral column. This technique has proved successful and meanwhile has come to be considered as state of the art.

Despite the development of new connecting techniques, such as the use of jaws with polyaxial bearings to connect the screws and the longitudinal rod, the intra-operative connection of the two elements remains problematic, particularly in cases of heavy spinal deformities. The problem lies in the fixed distance between the head of the pedicle screw and the longitudinal carrier. In other words, the polyaxial bearing of the screw head within the connecting jaw allows for variable screw angles but not for variable distances between the screw head and longitudinal rod carrier. A variable distance between the screw head or the end portion of the hook and the longitudinal rod carrier is desirable as it is not always possible to achieve 100 percent alignment of the vertebral column relative to the longitudinal rod.

It is accordingly an object of the invention to create an apparatus for connecting a pedicle screw or a pedicle hook to a longitudinal rod which provides a polyaxial bearing for the pedicle screw or pedicle hook and also provides a pivotable connection between the connector and the longitudinal rod, pivotable connection being lockable in any desired position.

SUMMARY OF THE INVENTION

The invention relates to a device for connecting a bone fastener to a longitudinal rod. The device comprises a connector with a coupling portion having two bores. Each bore has a longitudinal axis, and the axes are separated by a predetermined distance. The connector also has a holding member associated with the first bore and configured to engage the bone fastener to connect the fastener to the coupling. A rod coupler is associated with the second bore and comprises a bore engaging portion, a rod receiving portion and a locking member having a rod coupler engaging portion. The connector is configured so the rod and rod coupler may be rotated about the first bore longitudinal axis. In one embodiment, the holding member may be rotated about the second bore axis. In another embodiment, the rod coupler may be rotated about the second bore longitudinal axis. In yet another embodiment, the first and second bore axes are substantially parallel.

The holding member may comprise top and bottom surfaces and a wall having at least one vertical slot, the slot intersecting either the top or bottom surface. The holding member may have a bore configured to engage a bone fastener, and may also have locked and unlocked positions. A tensioner may be provided to engage the holding member bore to lock the holding member, rendering the holding member immobilized with respect to the coupler first bore, and immobilizing the bone fastener within the holding member.

The holding member and tensioner are configured so that when the tensioner engages the holding member to render it locked, the longitudinal rod and rod coupler may rotate 360 degrees within the second bore. In one embodiment, the tensioner may comprise the head of a bone fastener such as a bone screw or pedicle hook. Alternately, the holding member may comprise the head of a bone fastener.

The coupling portion first bore may comprise a substantially spherical inner surface and the holding member may comprise a correspondingly substantially spherical outer surface configured to slide within the inner surface. This configuration allows the holding member to rotate within the first bore about multiple axes, which may include axes both parallel and perpendicular to the first bore axis.

The holding member bore may have a conical profile and internal threads, and the tensioner may have a corresponding conical outer profile and external threads which mate with those of the bore. The holding member may be resiliently displaceable so that upon engagement with the tensioner, the holding member outer spherical surface may expand to engage the coupling first bore inner surface, configuring the holding member in the locked position. The holding member may have at least one slot configured to render the holding member resiliently displaceable.

The rod receiving portion may have at least one vertical leg configured to accept the longitudinal rod, and the rod coupling may have locked and unlocked positions. The rod coupler and holding member may, independent of each other, be configured in their respective locked or unlocked positions.

The rod receiving portion may comprise a channel having a longitudinal axis, a top distal from the bore engaging portion, and a bottom end opposite the top end. The channel longitudinal axis may be coaxial with that of the rod receiving portion. The top end of the channel may be open to allow a longitudinal rod to be introduced into the receiving portion by pressing the rod into the channel top end in a direction substantially parallel to the second bore axis.

The rod coupler bore engaging portion may comprise a bottom end having an increased portion having a dimension greater than that of the second bore, preventing the rod coupler from passing all the way through the coupling when the coupler is inserted into the bore. This increased portion may comprise a conical flange, and the second bore may have a corresponding conical recess adjacent the bottom surface of the coupling. The conical flange and recess may have corresponding engagement surfaces, and at least one of the engagement surfaces may have serrations to prevent relative movement of the flange and coupling bore.

An alternate embodiment of the connector may be provided for connecting a bone screw to a rod, the connector having a coupling with first and second bores separated by a predetermined distance, each bore having a longitudinal axis. A holding member may be associated with the first bore, and may be capable of engaging a bone screw. A rod coupler may be associated with the second bore, and may have a bore engaging portion and a rod receiving portion. The rod coupler may be rotatable about the second bore longitudinal axis.

The holding member and coupling first bore may have corresponding spherical surfaces configured to allow the holding member to rotate within the first bore about multiple axes.

The connector may also have a tensioner which may engage the holding member and immobilize the bone screw with respect to the holding member. The connector may be configured so that when the holding member engages the bone screw and the tensioner engages the holding member, and the rod coupler engages the longitudinal rod, the rod and rod coupler may be rotated 360 degrees within the second bore.

The rod coupler may be provided with first and second vertical legs to receive a longitudinal rod. A rod locking member may also be provided to engage a top portion of each of the first and second legs to retain the rod within the rod coupler along a direction perpendicular to a longitudinal axis of the rod. The rod locking member may have threads which engage corresponding threads in top portion of at least one of the first and second vertical legs of the rod coupler.

The first and second legs may each have a top end distal from the coupling, where the top ends are open to allow a rod to be introduced into the rod receiving portion by pressing the rod between the legs in a direction substantially parallel to the second bore axis. The rod receiving portion of the rod coupler may form a channel configured to allow a rod to be introduced into the rod receiving portion by threading the rod into the channel in a direction substantially perpendicular to the second bore axis.

The connector may also have a tensioner configured to engage the holding member to immobilize the bone screw with respect to the bone screw. The holding member may be radially expandable so that when engaged by the tensioner, the holding member spherical surface expands to engage the inner surface of the coupling first bore, thus locking the holding member to the coupling.

The rod locking member and rod coupler of this embodiment may be configured to engage the rod so that the rod may not move with respect to the rod coupler or rod locking member. The rod locking member and rod coupler may also be configured so that the rod is held between the rod locking member and a top surface of the connector. The rod coupler bore engaging portion may comprise a bottom end having an increased portion having a dimension greater than that of the second bore, wherein when the rod coupler is inserted into the second bore, the increased portion prevents the rod coupler from passing through the coupling. The increased portion may comprise a conical flange, and the second bore may have a corresponding conical recess adjacent to a bottom surface of the coupling. The conical flange and conical recess may have corresponding engaging surfaces, at least one of which may have serrations to prevent relative movement between the flange and bore.

The rod coupler bore engaging portion may further comprise a top end opposite the bottom end, the bore engaging portion further may comprise a second increased portion located at a point between the bore engaging portion top and bottom ends, the second increased portion having a dimension greater than that of the second bore, wherein when the rod coupler is inserted into the second bore, the first and second increased portions couple the rod coupler to the second bore. The rod coupler bore engaging portion may have at least one slot between the first and second increased portions, the at least one slot making at least part of the bore engaging portion resiliently displaceable to allow the second increase portion to be accepted within the second bore.

In yet another embodiment of the invention, a connector may be provided for connecting a bone screw to a rod, the connector having a coupling portion with first and second bores, each bore having a longitudinal axis, the axes separated by a predetermined distance, the first bore being associated with the bone screw. The connector also has a rod coupler associated with the second bore, the coupler having an articulating portion and a rod receiving portion. The articulating portion is configured to be rotatably and axially slidably receivable within the second bore. The rod receiving portion has at least one vertical leg configured to receive the rod in a direction substantially perpendicular to the second bore longitudinal axis. When the rod engages the rod coupler, the rod may be selectively rotated about the first bore longitudinal axis. The rod coupler may comprise a cap configured to engage the top end of the at least one vertical leg to retain the longitudinal rod in at least one direction perpendicular to the rod longitudinal axis.

The connector of this embodiment may further comprise a holding member associated with the first bore and configured to receive the bone screw. The holding member may have a bore configured to accept the bone screw, the holding member further having an unlocked position in which it is free to rotate within the first bore, and a locked position in which it is immobilized within the first bore. A tensioner may be provided to engage the holding member and configure the holding member in the locked position whereby the holding member is immobilized within the first bore. The tensioner may comprise external threads configured to engage internal threads of the holding member bore.

The connector is configured such that when the holding member engages the bone fastener, the tensioner engages the holding member, and the rod coupler engages the rod, the rod and rod coupler may be rotated 360 degrees about both the first and second bore longitudinal axes.

The first bore of the connector may have a substantially spherical inner surface and the holding member may have a substantially spherical outer surface configured to be slidably received within the first bore. The holding member may further be radially expandable such that when the tensioner engages the holding member bore, the holding member spherical outer surface expands to engage the inner spherical surface of the coupling first bore, thus locking the holding member to the coupling.

The holding member bore may have a conical profile and internal threads, and the tensioner may have a conical outer profile and external threads corresponding to the holding member bore.

The rod coupler may comprise a channel having a top end distal from the coupling portion and a bottom end proximal to the coupling portion, the channel top end being open to allow a rod having an axis substantially parallel to the channel axis to be introduced into the rod engaging portion by pressing the rod through the channel top end in a direction substantially parallel to the second bore axis.

The connector articulating portion may comprise an increased portion having a dimension greater than that of the second bore, such that when the rod coupler is inserted into the second bore, the increased portion prevents the rod coupler from passing through the coupling. The increased portion may comprise a conical flange, and the second bore may have a corresponding conical recess adjacent to the coupling portion bottom surface. The conical flange and bore may have corresponding engagement surfaces, and at least one engagement surface comprises serrations to prevent relative rotation between the flange and bore.

The holding member may have top and bottom surfaces and a wall. The wall may have at least one vertical slot intersecting at least the jaw top surface so that when the tensioner engages the holding member, the holding member expands along the at least one slot.

BRIEF DESCRIPTION OF THE DRAWINGS

The features and advantages of the present invention will become more readily apparent from the following detailed description of the invention in which like elements are labeled similarly, and in which:

FIG. 2 is a sectional view of a second embodiment of the invention of FIG. 1, showing the fastener holding member formed integrally with a bone fastener; and providing further illustration of a tensioner, holding member expansion feature, and longitudinal rod coupler;

FIG. 3 is a sectional view of a third embodiment of the present invention, showing the fastener holding member formed integrally with a pedicle hook.

DETAILED DESCRIPTION OF THE PREFERRED EMBODIMENTS

Figure 1:
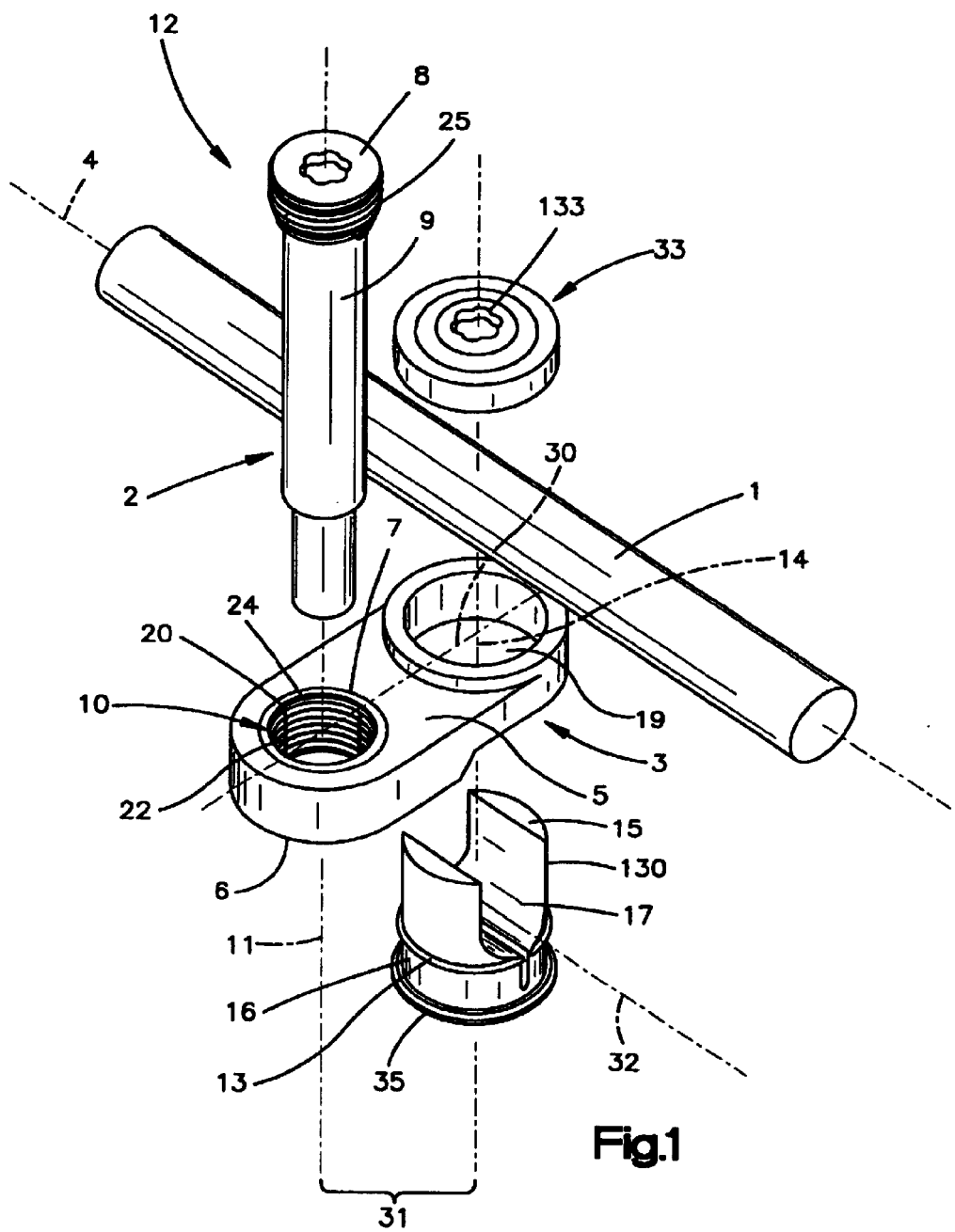
FIG. 1 is an exploded view of the first embodiment of the current invention.

FIGS. 1 and 2 show a coupling 3, a fastener holding member 10 having a tensioner 12 for releasably fixing a bone fastener 2 to a longitudinal rod coupler 13 with a rod locking element 33 configured for releasably fixing a longitudinal rod 1 to the coupling 3. The coupling 3 has a longitudinal axis 30, a top surface 5 configured to contact the longitudinal rod 1, a bottom surface 6, and a fastener coupling bore 7 which connects the top and bottom surfaces 5, 6. Fastener coupling bore 7 further has an axis 11 that is substantially perpendicular to the coupling longitudinal axis 30. In addition, the coupling 3 has a rod coupling bore 19 which connects the coupling top and bottom surfaces 5, 6 and has an axis 14 which is substantially parallel to the fastener coupling bore axis 11. The fastener and rod coupling bores 7, 19 are separated by at a distance 31 measured along the coupling longitudinal axis 30.

The rod coupling bore 19 is configured to slidingly receive a cylindrical articulating portion 130 of longitudinal rod coupler 13 such that the coupler 13 may rotate within the bore 19, about the rod coupling bore axis 14. The bottom end portion 16 of the rod coupler 13 comprises an increased-diameter flange portion 35, configured to mate with a corresponding recess 27 in the rod coupling bore 19, so that when the rod coupler articulating portion 130 is inserted into the rod coupling bore 19, the coupler flange portion 35 axially engages the rod coupler recess 27, preventing further axial movement of the rod coupler 13 with respect to the coupling 3 in the insertion direction.

The fastener coupling bore 7 may comprise a partial spherical profile, the top and bottom portions of the sphere being intersected and cut by coupling 3 top and bottom surfaces 5,6. The fastener holding member 10 may have a partial spherical outer surface profile designed to correspond to the fastener coupling bore 7 inner surface. The corresponding spherical surfaces allow the fastener holding member 10 to be received in the fastener coupling bore 7 so that the holding member 10 is fully pivotable within the bore (i.e., it may rotate about any one of, or combination of, three orthogonal axes).

The fastener holding member 10 may further comprise top and bottom surfaces 20, 21 positioned adjacent the coupling 3 top and bottom surfaces 5, 6 respectively. The holding member 10 may further comprise a conical bore 23 having an axis 230, when installed, concentric to the fastener coupling bore axis 11 and including a conical internal screw thread 24.

The fastener holding member 10 further may be configured so that its angular position within the fastener coupling bore 7 is lockable. Such a configuration may allow the user to lock the position of the associated fastener 2 in the desired pivot position, immobilizing it with respect to the coupling 3. This locking feature may be effected by providing a radial expansion feature within the holding member 10, so that when the desired holding member/fastener position is obtained at least a portion of the holding member 10 spherical surface may be expanded to contact or interfere with the fastener coupling bore 7, the frictional contact between surfaces preventing further relative movement. This radial expansion feature may be provided in the form of at least one vertical slot 101 located in the holding member 10, between the holding member outer spherical surface and conical bore surface 23. The at least one slot 101 may extend along a portion of the height of the holding member 10, and may be parallel to the holding member bore axis 230. The slot or slots 101 may intersect the top end surface 20 of the holding member 10, but not the bottom end surface 21. Alternatively the slot or slots 101 may intersect the bottom end surface 20 but not the top end surface 21. In one embodiment, the fastener holding member 10 comprises a series of parallel vertical slots evenly spaced about the circumference of the holding member 10, each slot intersecting one of the top or bottom end surfaces 20, 21 of the holding member 10.

A tensioner 12 may be provided to radially expand the holding member 10 to its aforementioned locked position. The tensioner 12 may comprise a frustoconical outer surface 120 corresponding to the holding member conical bore 23 and further may be provided with a conical external screw thread 25 corresponding to the holding member bore threads 24. The tensioner 12 may have an adjustment end 121 and a leading end 122, the adjustment end 121 comprising a connection 123 suitable for engagement with a standard driving tool. Due to the conical shape of the tensioner 12, the adjustment end 121 has a larger outer diameter than the leading end 122. Under this arrangement, the holding member 10 may be expanded by threadably driving the tensioner 12 into the bore so that the larger diameter adjustment end 121 enters a relatively smaller diameter portion of the holding member conical bore 23, forcing open the at least one vertical slot 101 in the holding member 10. Such expansion of the at least one slot 101 may be sufficient to press the holding member 10 outer surface against the fastener coupling bore 7, fixing the holding member 10 to the coupling bore 7, and coupling 3, as previously described.

In one embodiment, the tensioner 12 itself comprises the head portion 8 of the bone fastener 2. In an alternate embodiment, the holding member 10 comprises the head portion 8 of the bone fastener 2. The bone fastener 2 may be a bone screw 9 or a pedicle hook 90. Where the tensioner 12 is integral to the head portion 8 of the bone fastener 2, the bone fastener 2 may be releasably fixed to the coupling 3 by threadably driving the head portion 8 into the holding member 10, the corresponding conical surfaces 23, 120, threads 24, 25 and at least one slot 101 serving to expand the holding member 10 and fix the fastener 2 to the fastener coupling bore 7.

A longitudinal rod coupler 13 is used to receive and engage the longitudinal rod 1. The rod coupler 13 may have an articulating portion 130 that is configured to be rotatable and axially slidable within rod coupling bore 19, and which has an axis 131 that, when the coupler 13 is engaged with the coupling 3, is substantially coaxial to the rod coupling bore axis 14. The rod coupler 13 may also have a rod receiving portion 132 which, in one embodiment, comprises a channel 17 having a channel axis 32 oriented substantially perpendicular to the rod coupling bore axis 14. The channel 17 may have at least one vertical leg 133 configured to retain the longitudinal rod in at least a direction substantially perpendicular to the rod longitudinal axis 4.

The longitudinal rod coupler 13 may have a top end 15, adjacent to which channel 17 is open. The longitudinal rod coupler 13 may also have a bottom end 16 opposite the top end 15, and adjacent to the coupling bottom surface 6. The bottom end 16 may comprise an increased portion 35 having a diameter greater than the diameter of the rod coupling bore 19, so that when the rod coupler 13 is inserted into the rod coupling bore 19, the increased portion 35 prevents the rod coupler 13 from passing through the coupling bore 19 completely. Where the bottom end 16 comprises an increased portion 35, the bottom surface 6 of the coupling 3 may comprise a corresponding recess 27 configured to engage the increased portion 35. In one embodiment, the increased portion may comprise a conical flange 26, and the coupling 3 may comprise a correspondingly conical recess 27. To prevent post-installation rotation between the coupling 3 and the longitudinal rod coupler 13, at least one of the conical flange 26 or coupling recess 27, or both, may comprise serrations 28.

The channel 17 may be configured so that it is open at the top end 15 of the longitudinal rod coupler 13. To capture the longitudinal rod 1 within the rod coupler channel 17, a rod locking element 33. In one embodiment, the rod locking element 33 comprises a locking cap 133 may be provided. This cap 133 may comprise internal threads 134 configured to engage corresponding external threads 34 formed in the top end 15 of the rod coupler 13. Upon insertion of the longitudinal rod 1 in the channel 17, the locking cap 133 may be threaded onto the coupler top end 15 and rotated until a bottom surface 135 of the cap engages the longitudinal rod 1, thereby sandwiching the longitudinal rod 1 between the cap 133 and the top surface 5 of the coupling 3. To release the longitudinal rod 1, the locking cap 133 may be unscrewed and disengaged from the rod coupler top end 15.

In one embodiment, the portion of the coupling 3 comprising the fastener coupling bore 7 is recessed so that when a longitudinal rod 1 is engaged with the coupling 3, and a bone fastener 2 and tensioner 12 are fully engaged in the holding member 10, the fastener, tensioner and holding member are sufficiently recessed within the coupling 3 that the coupling 3 and rod 1 may be rotated without interference 360 degrees about the rod coupling bore axis 14.

FIG. 2 shows an alternative embodiment in which the fastener holding member 10 comprises the head portion 8 of the bone fastener 2, which, in this embodiment, is a bone screw 9. In this embodiment, the bottom end 16 of longitudinal rod coupler 13 comprises a conical flange 26, configured to be received in a complementary inner cone 27 formed in the rod coupling bore 19 of the coupling 3. Additionally, an at least partially circumferential tab segment 29 is provided on the rod coupler articulating portion adjacent the channel. This tab segment is adapted to engage the top surface 5 of the coupling 3 when the rod coupler is inserted into the rod coupling bore 14. When the tab segment 29 engages the top surface 5 of the coupling 3, it fixes the rod coupler 13 axially with respect to the coupling 3 and prevents the rod coupler 13 from backing out of the rod coupling bore 19. The inner diameter of the rod coupling bore 19 may be only slightly larger than the outer diameter of the articulating portion 130. The articulation portion 130 may, therefore, comprise at least one vertical slot 36 to allow the articulating portion 130 to be compressed so that the tab segment 29 can pass through the bottom surface 6 of the coupler and though the bore 19.

FIG. 3 shows an alternative embodiment of the rod coupler 13 in which the holding member 10 comprises the head portion 8 of the bone fastener 2, which, in this embodiment, is a pedicle hook 90. In this embodiment the head portion of the pedicle hook 90 comprises the spherically-shaped holding member 10.

Figure 4:
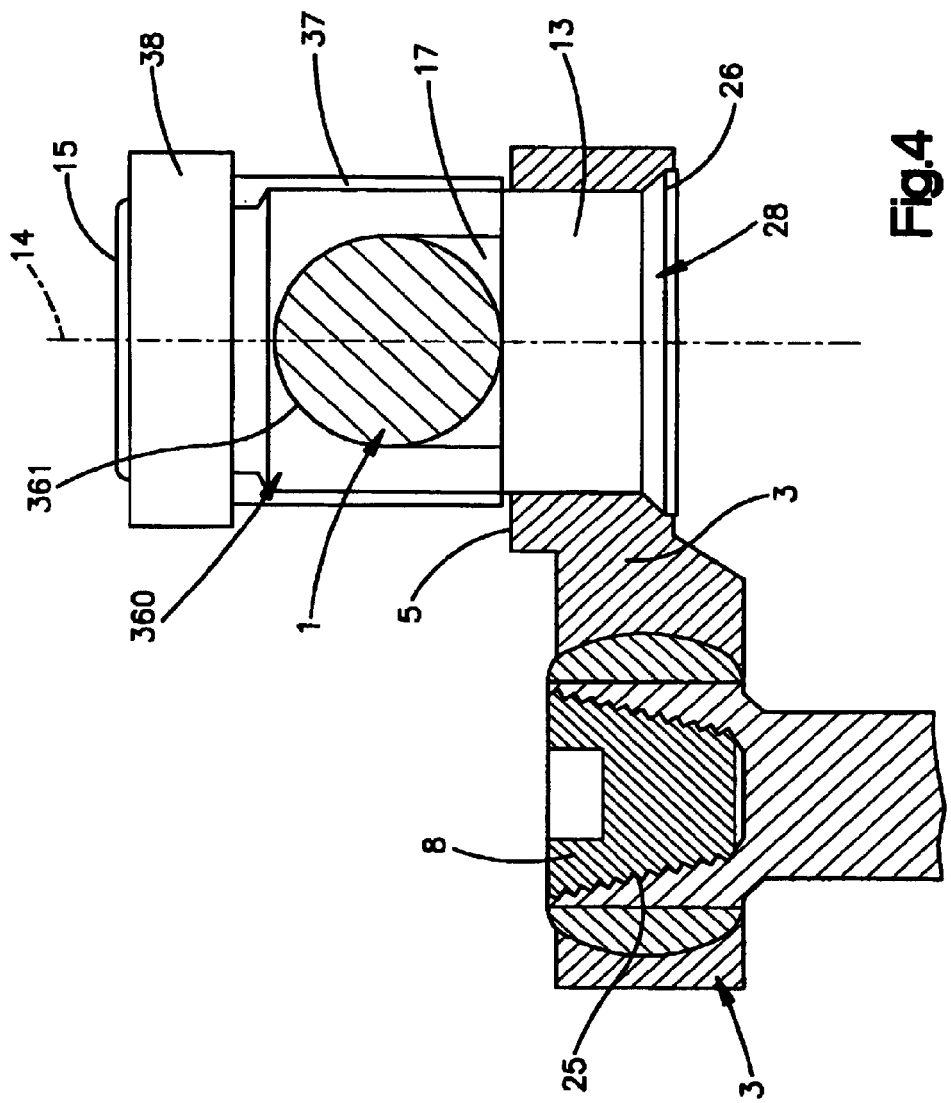
FIG. 4 is a sectional view of a fourth embodiment of the present invention, showing an alternate arrangement of the longitudinal rod coupler.

FIG. 4 shows a further embodiment of the coupling 3 in which channel 17 is open at the top end 15 to permit the longitudinal rod 1 to be inserted laterally into the longitudinal rod coupler 13 (i.e. in a direction perpendicular to the rod longitudinal axis 4). A sleeve 360, including a rod engaging surface 361, and two side walls 37 extending parallel to the rod coupling bore axis 14, is placed over the rod receiving portion 132 (in this case channel 17) at the top end 15 to fix the longitudinal rod 1 relative to the longitudinal rod coupler 13. The sleeve 360 is then held in place by a nut 38 which may be screwed onto an external screw thread 34 on the channel top end 15. Thus the longitudinal rod 1 is retained between the top surface 5 of the coupling 3 and the rod engaging surface 361 of the sleeve 360. The side walls 37 provide lateral fixation. In this embodiment, the conical flange 26 comprises radially aligned teeth (i.e., serrations, 28 which secure the rod coupler 13 and coupling 3 against relative rotational movement.

Accordingly, it should be understood that the embodiments disclosed herein are merely illustrative of the principles of the invention. Various other modifications may be made by those skilled in the art that will embody the principles of the invention and fall within the spirit and the scope thereof.

What is claimed is:

1. A connector for connecting a bone fastener to at rod, comprising:

a coupling portion having a top surface, a bottom surface and first and second bores, each bore having a longitudinal axis, the axes separated by a predetermined distance;

a holding member associated with the first bore arid configured to engage the bone fastener to connect the bone fastener to the coupling portion; the holding member having a top surface, a bottom surface, a wall extending from the top surface to the bottom surface, at least one vertical slot disposed in the wall and intersecting one of the top and bottom surfaces, and a bore extending therethrough sized and configured to accept the bone fastener, the holding member further having a locked position and an unlocked position;

a rod coupler associated with the second bore and comprising a bore engaging portion, a rod receiving portion having an axis, a locking member having a rod coupler engaging portion and a substantially circumferential tab segment, wherein the bore engaging portion has a bottom end with an increased portion having a dimension greater than that of the second bore so that when the rod coupler is inserted into the second bore, the increased portion prevents the rod coupler from passing through the coupling portion and the tab segment contacts the top surface of the coupling portion when the rod coupler is inserted into the second bore so that the rod coupler is axially fixed with respect to the coupling portion; and a tensioner sized and configured to be received within the bore formed in the holding member, the tensioner configured to engage the holding member to secure the holding member in the locked position whereby the holding member is immobilized with respect to the coupling portion and the bone fastener is immobilized within the holding member;

wherein the rod and rod coupler are selectively rotatable about the first bore longitudinal axis.

2. The connector of claim 1, wherein the holding member may be rotated about the second bore longitudinal axis.

3. The connector of claim 1, wherein the rod coupler may be rotated about the second bore longitudinal axis.

4. The connector of claim 1, wherein the first and second bore longitudinal axes are substantially parallel.

5. The connector of claim 1, wherein when the tensioner engages the holding member to configure the holding member in the locked position, the longitudinal rod and rod coupler may be rotated 360 degrees within the second bore.

6. The connector of claim 1, wherein the tensioner comprises a head portion of the bone fastener.

7. The connector of claim 1, wherein the coupling portion first bore comprises a substantially spherical inner surface and the holding member comprises a substantially spherical outer surface configured to slide within the spherical bore inner surface so that the holding member may rotate within the first bore about multiple axes.

8. The connector of claim 7, wherein the holding member may slide within the spherical bore inner surface about axes both parallel and perpendicular to the first bore axis.

9. The connector of claim 7, wherein the holding member bore has a conical profile and internal threads, the tensioner further comprising a conical outer profile and external threads corresponding to the bore.

10. The connector of claim 9, the holding member configured to be resiliently displaceable so that when the tensioner engage the bore the holding member outer spherical surface may expand to engage the coupling first bore inner spherical surface, configuring the holding member in the locked position.

11. The connector of claim 1, wherein the rod receiving portion has at least one vertical leg configured to accept the longitudinal rod, the rod coupler further having locked and unlocked positions.

12. The connector of claim 1, wherein the rod coupler also has a locked position and an unlocked position, wherein the rod coupler and the holding member are, independently positionable between their respective locked or unlocked positions.

13. The connector of claim 1, wherein the holding member comprises a head portion of the bone fastener.

14. The connector of claim 1, wherein the rod receiving portion of the rod coupler comprises a channel having a longitudinal axis, a top end distal from the bore engaging portion and a bottom end opposite the top end, the channel longitudinal axis coaxial with the rod receiving portion axis, the channel top end being open to allow a rod to be introduced into the rod receiving portion by pressing the rod through the channel top end in a direction substantially parallel to the second bore axis.

15. The connector of claim 1, wherein the increased portion comprises a conical flange, the second bore further comprises a corresponding conical recess adjacent to a bottom surface of the coupling portion.

16. The connector of claim 15 wherein the conical flange and conical recess have corresponding engagement surfaces, and at least one of the engagement surfaces comprises serrations configured to prevent relative rotation between the flange and the bore.

* * * * *